(12) United States Patent
Joshi et al.

(10) Patent No.: US 10,507,174 B2
(45) Date of Patent: Dec. 17, 2019

(54) SKIN CARE COMPOSITIONS

(71) Applicant: Rohm and Haas Company, Collegeville, PA (US)

(72) Inventors: Kinjalbahen Joshi, Collegeville, PA (US); Fanwen Zeng, Audubon, PA (US); Beth Cooper, Doylestown, PA (US)

(73) Assignee: Rohm and Haas Company, Philadelphia, PA (US)

(*) Notice: Subject to any disclaimer, the term of this patent is extended or adjusted under 35 U.S.C. 154(b) by 0 days.

(21) Appl. No.: 15/756,331

(22) PCT Filed: Aug. 24, 2016

(86) PCT No.: PCT/US2016/048257
§ 371 (c)(1),
(2) Date: Feb. 28, 2018

(87) PCT Pub. No.: WO2017/058404
PCT Pub. Date: Apr. 6, 2017

(65) Prior Publication Data
US 2018/0280280 A1    Oct. 4, 2018

Related U.S. Application Data

(60) Provisional application No. 62/233,480, filed on Sep. 28, 2015.

(51) Int. Cl.
| | | |
|---|---|---|
| *A61K 8/29* | (2006.01) | |
| *A61K 8/81* | (2006.01) | |
| *A61Q 17/04* | (2006.01) | |
| *A61K 8/02* | (2006.01) | |

(52) U.S. Cl.
CPC .......... *A61K 8/8152* (2013.01); *A61K 8/0279* (2013.01); *A61K 8/29* (2013.01); *A61Q 17/04* (2013.01)

(58) Field of Classification Search
None
See application file for complete search history.

(56) References Cited

U.S. PATENT DOCUMENTS

| | | |
|---|---|---|
| 5,663,213 A | 9/1997 | Jones et al. |
| 6,384,104 B1 | 5/2002 | Chang et al. |
| 6,576,051 B2 | 6/2003 | Bardman et al. |
| 6,710,161 B2 | 3/2004 | Bardman et al. |
| 7,081,488 B2 | 7/2006 | Bardman et al. |
| 7,179,531 B2 | 2/2007 | Brown et al. |
| 7,265,166 B2 | 9/2007 | Gebhard et al. |
| 2004/0091444 A1* | 5/2004 | Loffler ................ A61K 8/8158 424/70.17 |

OTHER PUBLICATIONS

Yau, et al; Modern Size-Exclusion Liquid Chromatography; Wiley; pp. 419-447; 1979.
Sibilia; A Guide to Materials Characterization and Chemical Analysis; VCH Publishers; pp. 81-84; 1988.

* cited by examiner

*Primary Examiner* — Jennifer A Berrios

(57) ABSTRACT

Provided are skin care compositions that are useful as SPF and UV absorption boosters in formulations containing inorganic metal oxides. The compositions comprise (a) (a) copolymer particles; (b) voided latex particles; (c) inorganic metal oxide particles; and (d) one or more dermatologically acceptable carriers. Also provided are methods of protecting skin from UVA and UVB damage comprising topically administering such compositions to the skin, and methods of boosting the SPF or UV absorption of a sunscreen composition containing inorganic metal oxide particles comprising including such copolymer particles and voided latex particles in the composition.

9 Claims, No Drawings

SKIN CARE COMPOSITIONS

FIELD

This invention relates generally to skin care compositions containing copolymer particles bearing phosphorus acid groups, voided latex particles, and inorganic metal oxide particles, and to methods of using the compositions for the protection of skin from UV damage.

BACKGROUND

Skin care compositions contain a variety of additives that provide an array of benefits to the composition. Sunscreen compositions (including compositions that provide sunscreen protection benefits, such as certain cosmetics and creams), for instance, contain additives that offer protection from ultraviolet ("UV") radiation, which can damage the skin. UV radiation can be classified as UVA (long wave; i.e., wavelengths of 320-400 nm) and UVB (short wave; i.e., wavelengths of 290 to 320 nm). The efficacy of a sunscreen formulation is measured by its sun protection factor ("SPF"). Since both UVA and UVB forms of radiation are harmful, sunscreen formulations preferably offer protection from both kinds of rays. Inorganic metal oxide particles, such as titanium dioxide and zinc oxide, provide absorption of UVA and UVB radiation and to this end are commonly incorporated into sunscreen formulations. Inorganic metal oxides, however, can cause negative aesthetic qualities such as poor sensorial feel and an undesirable white appearance, both of which may be due to agglomeration of particles and poor distribution on skin.

There is a need to develop new skin care compositions, such as sunscreen formulations, that contain sunscreen boosters which will help provide a high SPF, while improving aesthetic qualities of such formulations such as sensorial feel and visual appearance.

STATEMENT OF INVENTION

We have now found that a polymer combination, containing a phosphorus based copolymer and voided latex particles, is capable of enhancing the efficacy of inorganic metal oxides while also improving the aesthetic qualities, e.g., sensorial feel and visual appearance, of skin care compositions when applied to the skin. Advantageously, therefore, when the polymer combination is present in a skin care composition containing inorganic metal oxides, the polymer boosts the SPF of the inorganic metal oxides, thus providing greater UV blocking efficiency. Moreover, in some embodiments as described herein, the two polymers of the polymer combination act synergistic in boosting the efficacy of the inorganic metal oxides. That is, the polymers, in combination, are more effective than would be expected from their individual performance.

In one aspect, therefore, the invention provides a skin care composition. The skin care composition comprises:
  (a) copolymer particles comprising, based on the total weight of the copolymer particles, polymerized units derived from
    (i) 0.1 to 20 weight % of phosphorus acid monomers, and
    (ii) 80 to 99.9 weight % of comonomers;
  (b) voided latex particles comprising:
    (i) at least one core polymer comprising polymerized units derived from (a) 20 to 60 weight % of monoethylenically unsaturated monomers containing at least one carboxylic acid group, based on the total weight of the core polymer(s), and (b) 40 to 80 weight % of non-ionic ethylenically unsaturated monomers, based on the total weight of the core polymer(s); and
    (ii) at least one shell polymer comprising polymerized units derived from (a) 55 to 85 weight % of non-ionic ethylenically unsaturated monomers, based on the total weight of the shell polymer(s), and (b) 15 to 45 weight % of polyethylenically unsaturated monomers, based on the total weight of the shell polymer(s),
    wherein the voided latex particles contain a void and have a particle size of from 50 nm to 1000 nm;
  (c) inorganic metal oxide particles; and
  (d) one or more dermatologically acceptable carriers.

In another aspect the invention provides a method of protecting skin from UVA and/or UVB damage. The method comprises topically administering to the skin a skin care composition as described herein.

In a further aspect, the invention provides a method of boosting the SPF or UV absorption of a skin care composition containing inorganic metal oxide particles and one or more dermatologically acceptable carriers. The method comprises including in the skin care composition copolymer particles and voided latex particles as described herein.

DETAILED DESCRIPTION

Unless otherwise indicated, numeric ranges, for instance as in "from 2 to 10," are inclusive of the numbers defining the range (e.g., 2 and 10). Unless otherwise indicated, ratios, percentages, parts, and the like are by weight. As used herein, unless otherwise indicated, the phrase "molecular weight" or Mw refers to the weight average molecular weight as measured in a conventional manner with gel permeation chromatography (GPC) and polyacrylic acid standards. GPC techniques are discussed in detail in Modern Size Exclusion Chromatography, W. W. Yau, J. J. Kirkland, D. D. Bly; Wiley-Interscience, 1979, and in A Guide to Materials Characterization and Chemical Analysis, J. P. Sibilia; VCH, 1988, p. 81-84. Molecular weights are reported herein in units of Daltons. The term "ethylenically unsaturated" is used to describe a molecule or moiety having one or more carbon-carbon double bonds, which renders it polymerizable. "Polymer" refers to a polymeric compound prepared by polymerizing monomers, whether of the same or a different type. The generic term "polymer" includes the terms "homopolymer," "copolymer," and "terpolymer." The term "polymerized units derived from" refers to polymer molecules that are synthesized according to polymerization techniques wherein a product polymer contains "polymerized units derived from" the constituent monomers which are the starting materials for the polymerization reactions. The term "ethylenically unsaturated" includes monoethylenically unsaturated (having one carbon-carbon double bond) and multi-ethylenically unsaturated (having two or more carbon-carbon double bonds). As used herein the term "(meth)acrylic" refers to acrylic or methacrylic and "(meth) acrylate" refers to either acrylate or methacrylate. Weight percentages (or wt %) in the composition are percentages of dry or actives weight, i.e., excluding any water that may be present in the composition. Percentages of monomer units in a polymer are percentages of solids or neat monomer weight, i.e., excluding any water present in a polymer emulsion, and are based on the total weight of the polymer (determined from the total weight of the monomers from which the polymer is comprised.

"Skin care compositions" refers to compositions for leave on application to the skin, such as lotions, creams, gels, gel creams, serums, toners, wipes, liquid foundations, make-ups, tinted moisturizer, oils, face/body sprays, topical medicines, and sunscreen compositions. The term encompasses multi-functional compositions that have, as at least one of their functions, protection of skin from UV damage and include, for instance, cosmetics and lotions that are intended to provide such protection. "Sunscreen compositions" refers to skin care compositions that are primarily directed at protecting the skin from UV damage.

Preferably, the skin care composition is cosmetically acceptable. "Cosmetically acceptable" and "dermatologically acceptable" are used interchangeably and refer to ingredients typically used in skin care compositions, and are intended to underscore that materials that are toxic when present in the amounts typically found in skin care compositions are not contemplated as part of the present invention. The compositions of the invention may be manufactured by processes well known in the art, for example, by means of conventional mixing, dissolving, granulating, emulsifying, encapsulating, entrapping or lyophilizing processes.

"Glass transition temperature" or "$T_g$" refers to the temperature at or above which a glassy polymer will undergo segmental motion of the polymer chain. Glass transition temperatures of a polymer can be estimated by the Fox equation (*Bulletin of the American Physical Society*, 1 (3) Page 123 (1956)) as follows:

$$1/T_g = w_1/T_{g(1)} + w_2/T_{g(2)}$$

For a copolymer, $w_1$ and $w_2$ refer to the weight fraction of the two comonomers, and $T_{g(1)}$ and $T_{g(2)}$ refer to the glass transition temperatures of the two corresponding homopolymers made from the monomers. For polymers containing three or more monomers, additional terms are added ($w_n/T_{g(n)}$). The $T_{(g)}$ of a polymer can also be calculated by using appropriate values for the glass transition temperatures of homopolymers, which may be found, for example, in "Polymer Handbook," edited by J. Brandrup and E. H. Immergut, Interscience Publishers. The $T_g$ of a polymer can also be measured by various techniques, including, for example, differential scanning calorimetry ("DSC"). The values of $T_g$ reported herein are measured by DSC.

As indicated above, in one aspect, the invention provides a skin care composition. The skin care composition contains copolymer particles comprising polymerized units derived from (i) 0.1 to 20 weight % of phosphorus acid monomers, and (ii) 80 to 99.9 weight % of comonomers, each based on the total weight of the copolymer particles.

The phosphorus acid monomers contain at least one ethylenic unsaturation and a phosphorus acid group. The phosphorus acid monomer may be in the acid form or as a salt of the phosphorus acid group. The term "phosphorus acid group" refers to a phosphorus oxo acid having a POH moiety in which the hydrogen atom is ionizable. Also included in the term "phosphorus acid group" are salts of the phosphorus oxo acid. In its salt or basic form, the phosphorus acid group has a cation such as a metal ion or an ammonium ion replacing at least one acid proton. Examples of phosphorus acid groups include groups formed from phosphinic acid, phosphonic acid, phosphoric acid, pyrophosphinic acid, pyrophosphoric acid, partial esters thereof, and salts thereof.

Suitable phosphorus acid monomers include, for example:

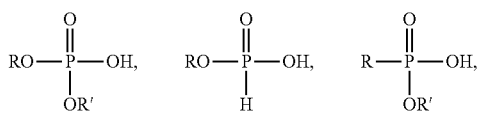

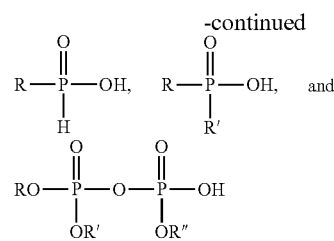

wherein R is an organic group containing an acryloxy, methacryloxy, or a vinyl group; and R' and R" are independently selected from H and a second organic group. The second organic group maybe saturated or unsaturated.

Further examples of suitable phosphorus acid monomers include dihydrogen phosphate-functional monomers, e.g., dihydrogen phosphate esters of an alcohol in which the alcohol also contains a polymerizable vinyl or olefinic group (e.g., allyl phosphate, mono- or diphosphate of bis(hydroxyl-methyl)fumarate or itaconate), and derivatives of (meth)acrylic acid esters, e.g., phosphates of hydroxyalkyl (meth)acrylates (e.g., 2-hydroxyethyl (meth)acrylate and 3-hydroxypropyl (meth)acrylates).

Other suitable phosphorus acid monomers include, for example, phosphonate functional monomers, e.g., vinyl phosphonic acid, allyl phosphonic acid, α-phosphonostyrene, and 2-methylacrylamido-2-methylpropanephosphonic acid. Further suitable phosphorus functional monomers include, for example, 1,2-ethylenically unsaturated (hydroxy)phosphinylalkyl (meth)acrylate monomers, e.g., (hydroxy)phosphinylmethyl methacrylate. In certain preferred embodiments, the phosphorus acid monomers comprise dihydrogen phosphate monomers, e.g., 2-phosphoethyl (meth)acrylate, 2-phosphopropyl (meth)acrylate, 3-phosphopropyl (meth)acrylate, and 3-phospho-2-hydroxypropyl (meth)acrylate.

The copolymers comprise polymerized units of the phosphorus acid monomers in an amount of at least 0.1 weight %, preferably at least 0.5 weight %, and more preferably at least 1 weight %, by weight of the copolymer and up to 20 weight %, preferably up to 10 weight %, and more preferably up to 6 weight %, based on the total weight of the copolymer.

The comonomers components of the copolymer are ethylenically unsaturated monomers which are not phosphorus acid monomers and are copolymerizable with an ethylenically unsaturated phosphorus acid monomer. Suitable comonomers include, for example, styrene, butadiene, α-methyl styrene, vinyl toluene, vinyl naphthalene, ethylene, propylene, vinyl acetate, vinyl versatate, vinyl chloride, vinylidene chloride, acrylonitrile, methacrylonitrile, (meth)acrylamide, various $C_1$-$C_{40}$ alkyl esters of (meth)acrylic acid (e.g., methyl (meth)acrylate, ethyl (meth)acrylate, n-butyl (meth)acrylate, 2-ethylhexyl (meth)acrylate, cyclohexyl (meth)acrylate, n-octyl (meth)acrylate, n-decyl (meth)acrylate, n-dodecyl (meth)acrylate, tetradecyl (meth)acrylate, lauryl (meth)acrylate, oleyl (meth)acrylate, palmityl (meth)acrylate, and stearyl (meth)acrylate)), and other (meth)acrylates (e.g., isobornyl (meth)acrylate, benzyl (meth)acrylate, phenyl (meth)acrylate, 2-bromoethyl (meth)acrylate, 2-phenylethyl (meth)acrylate, and 1-naphthyl (meth)acrylate)), alkoxyalkyl (meth)acrylates, e.g., ethoxyethyl (meth)acrylate, mono-, di-, trialkyl esters of ethylenically unsaturated di- and tricarboxylic acids and anhydrides (e.g., ethyl maleate, dimethyl fumarate, trimethyl aconitate, and ethyl methyl itaconate), and carboxylic acid containing monomers, e.g., (meth)acrylic acid, itaconic acid, fumaric acid, and maleic acid.

The inventive copolymers comprise polymerized units of comonomers in an amount of at least 80 weight %, preferably at least 90 weight %, and more preferably at least 94 weight %; and no more than 99.9 weight %, preferably no more than 99.5 weight %, and more preferably no more than 99 weight %, by weight based on the total weight of the copolymer.

In some embodiments, the copolymer may be a crosslinked polymer, wherein a crosslinker, such as a monomer having two or more non-conjugated ethylenically unsaturated groups, is included with the copolymer components during polymerization. Suitable crosslinker monomers include, for example, di- or tri-allyl ethers and di- or tri-(meth)acrylyl esters of diols or polyols (e.g., trimethylolpropane diallyl ether, ethylene glycol dimethacrylate), di- or tri-allyl esters of di- or tri-acids, allyl (meth)acrylate, divinyl sulfone, triallyl phosphate, divinylaromatics (e.g., divinylbenzene). In certain embodiments, the inventive copolymers comprise polymerized units of crosslinker monomers in an amount of no more than 5 weight %, preferably no more than 3 weight %, more preferably no more than 2 weight %, and even more preferably no more than 1 weight %, based on the total weight of the copolymer.

In some embodiments, the copolymer particles of the invention have a weight average molecular weight ($M_w$) of 5,000,000 or less, preferably 3,000,000 or less, more preferably 2,000,000 or less, and even more preferably 1,000,000 or less. In some embodiments, the copolymer particles have a $M_w$ of 5,000 or more, preferably 50,000 or more, and more preferably 100. Copolymer particles suitable for use in the inventive skin care compositions preferably have $T_g$ values in the range of from 25° C. to 150° C., preferably from 50° C. to 150° C., and more preferably from 60° C. to 100° C.

In some embodiments, the inventive copolymer particles have an average diameter in a range of from 10 nm to 20 microns, preferably from 20 nm to 1 micron, and more preferably from 50 nm to 500 nm. The diameters of the copolymer particles may be characterized by distributions such as unimodal or multimodal, including bimodal. The average diameter of the copolymer particles may be determined by a light scattering technique.

In some embodiments, the inventive skin care composition includes copolymer particles in an amount of from 0.1 to 30 weight %, preferably from 0.5 to 15 weight %, based on the total weight of the composition.

Suitable polymerization techniques for preparing the copolymer particles contained in the inventive skin care compositions include, for example, emulsion polymerization and solution polymerization, preferably emulsion polymerization, as disclosed in U.S. Pat. No. 6,710,161. Aqueous emulsion polymerization processes typically are conducted in an aqueous reaction mixture, which contains at least one monomer and various synthesis adjuvants, such as the free radical sources, buffers, and reductants in an aqueous reaction medium. In certain embodiments, a chain transfer agent may be used to limit molecular weight. The aqueous reaction medium is the continuous fluid phase of the aqueous reaction mixture and contains more than 50 weight % water and optionally one or more water miscible solvents, based on the weight of the aqueous reaction medium. Suitable water miscible solvents include, for example, methanol, ethanol, propanol, acetone, ethylene glycol ethyl ethers, propylene glycol propyl ethers, and diacetone alcohol. In certain embodiments, the aqueous reaction medium contains more than 90 weight % water, preferably more than 95 weight % water, and more preferably more than 98 weight % water, based on the weight of the aqueous reaction medium. In certain embodiments, the aqueous reaction medium has a pH of less than or equal to 8, and preferably having a pH of less than or equal to 4.

The polymerization process may be conducted as a batch, semicontinuous, or continuous process. In certain embodiments, the polymer is formed in a two stage reaction. In certain embodiments, the first stage comprises polymerizing 1 to 10 weight % of phosphorus acid monomers, 99 to 80 weight % comonomers, and 0 to 5 weight % of crosslinker, based on the total weight of monomers polymerized in the first stage. In certain embodiments, the second stage comprises polymerizing 95 to 100 weight % comonomers, and 0 to 5 weight % of crosslinker, based on the total weight of monomers polymerized in the second stage. In certain embodiments, the phosphorus acid monomers comprise a phosphoethyl methacrylate. In certain embodiments, the comonomers comprise at least one of butyl acrylate, methyl methacrylate, and methacrylic acid. In certain embodiments, the crosslinker comprises allyl methacrylate. In certain embodiments, the total ratio of monomers polymerized in stage 1 and stage 2 ranges from 20:80 to 80:20, preferably from 25:75 to 75:25, and more preferably from 30:70 to 70:30.

The inventive skin care compositions may contain the copolymer particles dispersed in an aqueous medium. The aqueous medium may contain cosolvents, e.g., water miscible cosolvents. Suitable water miscible cosolvents include, for example, methanol, ethanol, propanol, acetone, ethylene glycol ethyl ethers, propylene glycol propyl ethers, and diacetone alcohol; and water immiscible solvents such as propyl acetate, butyl acetate, methyl isoamyl ketone, amyl acetate, diisobutyl ketone, xylene, toluene, butanol, and mineral spirits. The pH of the skin care composition may be in the range of 3 to 11.

In some embodiments, the skin care composition is characterized as being substantially-free of water soluble phosphorus acid compounds. Water soluble phosphorus acid compounds contain phosphorus acid groups, referred to herein as "second phosphorus acid groups." At a pH of 5 and above, the water soluble phosphorus acid compounds are contained as a solubilized component of the aqueous medium. The water soluble phosphorus acid compounds include inorganic phosphorus acid compounds and organic phosphorus acid compounds. Inorganic phosphorus acid compounds include phosphorus oxo acids such as phosphoric acid, phosphorus acid, hydrophosphorous acid, orthophosphoric acid, pyrophosphoric acid, and salts thereof. Organic phosphorus acid compounds contain at least one phosphorus acid group attached to an organic moiety and include both unsaturated organic phosphorus acid compounds such as phosphorus acid monomers; and saturated organic phosphorus acid compounds such as partial esters of phosphorus oxo acids such as $HOCH_2CH_2OP(O)(OH)_2$, methyl phosphonic acid, and water soluble polymer bearing phosphorus acid groups. The water soluble polymer bearing phosphorus acid groups are addition polymers containing at least two phosphorus acid groups that are independently located pendant to the backbone of the water soluble polymer or in a terminal position. The water soluble polymer bearing phosphorus acid groups may be a homopolymer or a copolymer, and has a degree of polymerization of at least 2. As used herein, "saturated phosphorus acid compounds" are compounds selected from inorganic phosphorus acid compounds and saturated organic phosphorus acid compounds. As used herein, "substantially-free of water soluble phosphorus acid compounds" refers to a level of water soluble phosphorus acid compounds in the polymer composition as defined by the ratio of equivalents of second phosphorus acid groups to equivalents of first phosphorus acid groups in a range having an upper value of 0.8, preferably 0.7, and more preferably 0.5; and may have a lower value in the range of 0.1, preferably 0.05, and more preferably zero. In one embodiment, the ratio of equivalents of second phosphorus acid groups to equivalents of first phosphorus acid groups is in the range of less than or equal to 0.8, preferably less than or equal to 0.7, and more preferably less than or equal to 0.5. The ratio of equivalents of second phosphorus acid groups to equivalents of first phosphorus acid groups in the skin care composition is determined by inductively coupled plasma spectroscopy detection of phosphorus atoms, as disclosed in U.S. Pat. No. 6,710,161. The first phosphorus acid groups and the second phosphorus acid groups may be the same type of phosphorus acid or may be different; for example, the first phosphorus acid groups may be formed from phosphoric acid and the second phosphorus acid groups may be formed from phosphonic acid.

The skin care compositions of the invention contain voided latex particles. The voided latex particles comprise a multistaged particle containing at least one core polymer and at least one shell polymer. More specifically, the voided latex particles comprise: (i) at least one core polymer comprising polymerized units derived from (a) 20 to 60 weight % of monoethylenically unsaturated monomers containing at least one carboxylic acid group, based on the total weight of the core polymer, and (b) 40 to 80 weight % of non-ionic ethylenically unsaturated monomers, based on the total weight of the core polymer; and (ii) at least one shell polymer comprising polymerized units derived from (a) 55 to 85 weight % of non-ionic ethylenically unsaturated monomers, based on the total weight of the shell polymer(s), and (b) 15 to 45 weight % of polyethylenically unsaturated monomers, based on the total weight of the shell polymer(s). The voided latex particles contain a void and have a particle size of from 50 nm to 1000 nm. The ratio of the core weight to the total polymer weight of the voided latex particle is preferably from 1:4 (25% core) to 1:100 (1% core, and preferably from 1:8 (12% core) to 1:50 (2% core).

The at least one core polymer includes polymerized units derived from monoethylenically unsaturated monomers containing at least one carboxylic acid group, and non-ionic ethylenically unsaturated monomers. The core polymer may be obtained, for example, by the emulsion homopolymerization of the monoethylenically unsaturated monomer containing at least one carboxylic acid group or by copolymerization of two or more of the monoethylenically unsaturated monomers containing at least one carboxylic acid group. In certain embodiments, the monoethylenically unsaturated monomer containing at least one carboxylic acid group is copolymerized with one or more non-ionic (that is, having no ionizable group) ethylenically unsaturated monomers. While not wishing to be bound by theory, it is believed that the presence of the ionizable acid group makes the core swellable by the action of a swelling agent, such as an aqueous or gaseous medium containing a base to partially neutralize the acid core polymer and cause swelling by hydration.

Suitable monoethylenically unsaturated monomers containing at least one carboxylic acid group of the core polymer include, for example, (meth)acrylic acid, (meth) acryloxypropionic acid, itaconic acid, aconitic acid, maleic acid, fumaric acid, crotonic acid, citraconic acid, maleic anhydride, monomethyl maleate, monomethyl fumarate, and monomethyl itaconate, and other derivatives such as corresponding anhydride, amides, and esters. In certain preferred embodiments, the monoethylenically unsaturated monomers containing at least one carboxylic acid group are selected from acrylic acid and methacrylic acid. In certain embodiments, the core comprises polymerized units of monoethylenically unsaturated monomers containing at least one carboxylic acid group in an amount of from 20 to 60 weight %, preferably from 30 to 50 weight %, and more preferably from 35 to 45 weight %, based on the total weight of the core polymer.

Suitable non-ionic ethylenically unsaturated monomers of the core polymer include, for example, styrene, vinyltoluene, ethylene, vinyl acetate, vinyl chloride, vinylidene chloride, acrylonitrile, (meth)acrylamide, ($C_1$-$C_{22}$)alkyl and ($C_3$-$C_{20}$)alkenyl esters of (meth)acrylic acid, such as methyl (meth)acrylate, ethyl (meth)acrylate, butyl (meth)acrylate, 2-ethylhexyl (meth)acrylate, benzyl (meth)acrylate, lauryl (meth)acrylate, oleyl (meth)acrylate, palmityl (meth)acrylate and stearyl (meth)acrylate. In certain preferred embodiments, the non-ionic ethylenically unsaturated monomers are selected from methyl methacrylate and butyl methacrylate. In certain embodiments, the core comprises polymerized units of non-ionic ethylenically unsaturated monomers in an amount of from 40 to 80 weight %, preferably from 50 to 70 weight %, and more preferably from 55 to 65 weight %, based on the total weight of the core polymer.

The voided latex particles also include at least one shell polymer. The at least one shell polymer(s) comprise polymerized units derived from non-ionic ethylenically unsaturated monomers and polyethylenically unsaturated monomers. In certain embodiments, the at least one shell polymer optionally comprises polymerized units derived from monoethylenically unsaturated monomers containing at least one carboxylic acid group and monoethylenically unsaturated monomers containing at least one non-carboxylic acid group. In certain embodiments, the shell portion of the voided latex particles are polymerized in a single stage, preferably in two stages, and more preferably in at least three stages. As used herein, the term "outermost shell" refers to the composition of the final distinct polymerization stage used to prepare the voided latex particles. In certain embodiments wherein the outermost shell is provided by a multistage polymerization process, the outermost shell comprises at least 25 weight %, preferably at least 35 weight %, and more preferably at least 45 weight % of the total shell portion of the voided latex particle.

Suitable non-ionic ethylenically unsaturated monomers for the shell polymer(s) include, for example, vinyl acetate, acrylonitrile, methacrylonitrile, nitrogen containing ring compound unsaturated monomers, vinylaromatic monomers, ethylenic monomers and selected (meth)acrylic acid derivatives. Suitable (meth)acrylic acid derivatives include, for example, ($C_1$-$C_{22}$)alkyl (meth)acrylate, substituted (meth)acrylate, and substituted (meth)acrylamide monomers. In certain preferred embodiments, the (meth)acrylic acid derivatives are selected from methyl acrylate, methyl methacrylate, ethyl acrylate, ethyl methacrylate, butyl acrylate, butyl methacrylate, isobutyl acrylate, isobutyl methacrylate, hydroxyethyl methacrylate, hydroxypropyl methacrylate, dimethylaminoethyl methacrylate, dimethylaminopropyl methacrylamide, and mixtures thereof. Suitable vinylaromatic monomers include, for example, styrene, α-methylstyrene, vinyltoluene, alkyl-substituted styrene (such as t-butylstyrene and ethylvinylbenzene), and halogenated styrenes (such as chlorostyrene and 3,5-bis (trifluoromethyl)styrene). In certain preferred embodiments, the vinylaromatic monomers are selected from styrene, ethylvinylbenzene, t-butylstrene, and mixtures thereof. In certain embodiments, the shell polymer(s) comprise polymerized units of non-ionic ethylenically unsaturated monomers in an amount of from 55 to 85 weight %, preferably from 60 to 80 weight %, and more preferably from 65 to 75 weight %, based on the total weight of the shell polymer(s).

Suitable polyethylenically unsaturated monomers for the shell polymer(s) include, for example, di(meth)acrylates, tri(meth)acrylates, tetra(meth)acrylates, polyallylic monomers, polyvinylic monomers, and (meth)acrylic monomers having mixed ethylenic functionality. Suitable polyvinylic monomers include, for example, diethyleneglycol divinyl ether, divinylbenzene, divinyl ketone, divinylpyridine, divinyl sulfide, divinyl sulfone, divinyltoluene, divinylxylene, glycerol trivinyl ether, trivinylbenzene, 1,2,4-trivinylcyclohexane, N,N'-ethylenebisacrylamide, partially fluorinated α,ω-dienes (such as $CF_2{=}CFCF_2CF_2CH_2CH{=}CH_2$), trifluoroalkadienes, trifluorodivinylbenzenes, and fluorinated divinyl ethers of fluorinated 1,2-ethanediol. In certain preferred embodiments, the polyvinylic monomer comprises divinylbenzene. Suitable (meth)acrylic monomers having mixed ethylenic functionality include, for example, the acrylate ester of neopentyl glycol monodicyclopentenyl ether, allyl acryloxypropionate, allyl acrylate, allyl methacrylate, crotyl acrylate, crotyl methacrylate, 3-cyclohexenylmethyleneoxyethyl acrylate, 3-cyclohexenylmethyleneoxyethyl methacrylate, dicyclopentadienyloxyethyl acrylate, dicyclopentadienyloxyethyl methacrylate, dicyclopentenyl acrylate, dicyclopentenyl methacrylate, dicyclopentenyloxyethyl acrylate, dicyclo pentenyloxyethyl methacrylate, methacrylate ester of neopentyl glycol monodicyclopentenyl ether, methallyl acrylate, trimethylolpropane diallyl ether mono-acrylate, trimethylolpropane diallyl ether mono-methacrylate, and N-allyl acrylamide. In certain preferred embodiments, the (meth)acrylic monomers having mixed ethylenic functionality comprise allyl methacrylate. In certain embodiments, the shell polymer(s) comprise polymerized units of polyethylenically unsaturated monomers in an amount of from 15 to 45 weight %, preferably from 20 to 35 weight %, and more preferably from 22 to 30 weight %, based on the total weight of the shell polymer(s). In certain embodiments, the outermost shell comprises polymerized units of polyethylenically unsaturated monomers in an amount of from 10 to 100 weight %, preferably from 15 to 70 weight %, and more preferably from 20 to 60 weight %, based on the weight of the outermost shell polymer.

The optional monoethylenically unsaturated monomers containing at least one carboxylic acid group of the shell polymer(s) may include, for example, (meth)acrylic acid, (meth)acryloxypropionic acid, itaconic acid, aconitic acid, maleic acid, fumaric acid, crotonic acid, citraconic acid, maleic anhydride monomethyl maleate, monomethyl fumarate, and monomethyl itaconate, and other derivatives such as corresponding anhydride, amides, and esters. In certain preferred embodiments, the monoethylenically unsaturated monomers containing at least one carboxylic acid group are selected from acrylic acid and methacrylic acid. In certain embodiments, the shell polymer(s) comprises polymerized units of monoethylenically unsaturated monomers containing at least one carboxylic acid group in an amount of from 0.1 to 10 weight %, preferably from 0.3 to 7.5 weight %, and more preferably from 0.5 to 5 weight %, based on the total weight of the shell polymer(s).

The optional monoethylenically unsaturated monomers containing at least one non-carboxylic acid group for the shell polymer(s) may include, for example, allylsulfonic acid, allylphosphonic acid, allyloxybenzenesulfonic acid, 2-acrylamido-2-methylpropanesulfonic acid ("AMPS"), 2-hydroxy-3-(2-propenyloxy)propanesulfonic acid, 2-methyl-2-propene-1-sulfonic acid, 2-methacrylamido-2-methyl-1-propanesulfonic acid, 3-methacrylamido-2-hydroxy-1-propanesulfonic acid, 3-sulfopropyl acrylate, 3-sulfopropyl methacrylate, isopropenylphosphonic acid, vinylphosphonic acid, phosphoethyl methacrylate, styrenesulfonic acid, vinylsulfonic, acid and the alkali metal and ammonium salts thereof. In certain preferred embodiments, the monoethylenically unsaturated monomers containing at least one non-carboxylic acid group are selected from 2-acrylamido-2-methylpropanesulfonic acid, styrenesulfonic acid, and sodium styrene sulfonate. In certain embodiments, the shell polymer(s) comprise polymerized units of monoethylenically unsaturated monomers containing at least one "non-carboxylic" acid group in an amount of from 0.1 to 10 weight %, preferably from 0.5 to 7.5 weight %, and more preferably from 1 to 5 weight %, based on the total weight of the shell polymer(s).

The shell polymer(s) of the latex particles suitable for use in the present invention have $T_g$ values which are high enough to support the void within the latex particle. In certain embodiments, the $T_g$ values of at least one shell are greater than 50° C., preferably greater than 60° C., and more preferably greater than 70° C.

In certain embodiments, the core polymer and shell polymer are made in a single polymerization step. In certain other embodiments, the core polymer and shell polymer are made in a sequence of polymerization steps. Suitable polymerization techniques for preparing the voided latex particles contained in the inventive skin care compositions include, for example, sequential emulsion polymerization. Aqueous emulsion polymerization processes typically are conducted in an aqueous reaction mixture, which contains at least one monomer and various synthesis adjuvants, such as the free radical sources, buffers, and reductants in an aqueous reaction medium. In certain embodiments, a chain transfer agent may be used to limit molecular weight. The aqueous reaction medium is the continuous fluid phase of the aqueous reaction mixture and contains more than 50 weight % water and optionally one or more water miscible solvents, based on the weight of the aqueous reaction medium. Suitable water miscible solvents include, for example, methanol, ethanol, propanol, acetone, ethylene glycol ethyl ethers, propylene glycol propyl ethers, and diacetone alcohol.

In certain embodiments, the void of the latex particles is prepared by swelling the core with a swelling agent containing one or more volatile components. The swelling agent permeates the shell to swell the core. The volatile components of the swelling agent can then be removed by drying the latex particles, causing a void to be formed within the latex particles. In certain embodiments, the swelling agent is an aqueous base. Suitable aqueous bases useful for swelling the core include, for example, ammonia, ammonium hydroxide, alkali metal hydroxides, such as sodium hydroxide, or a volatile amine such as trimethylamine or triethylamine. In certain embodiments, the voided latex particles are added to the composition with the swelling agent present in the core. When the latex particles are added to the composition with the swelling agent present in the core, the volatile components of the swelling agent will be removed upon drying of the composition. In certain other embodiments, the voided latex particles are added to the composition after removing the volatile components of the swelling agent.

In certain embodiments, the voided latex particles contain a void with a void fraction of from 1% to 70%, preferably from 5% to 50%, more preferably from 10% to 40%, and even more preferably from 25% to 35%. The void fractions are determined by comparing the volume occupied by the latex particles after they have been compacted from a dilute dispersion in a centrifuge to the volume of non-voided particles of the same composition. The voided latex particles have a particle size of from 50 nm to 1000 nm, preferably 100 nm to 600 nm, preferably from 200 nm to 500 nm, preferably from 300 nm to 400 nm, more preferably from 400 nm to 600 nm, and even more preferably from 400 nm to 550 nm, as measured by a Brookhaven BI-90 photon correlation spectrometer.

A person of ordinary skill in the art can readily determine the effective amount of the voided latex particles that should be used in a particular composition in order to provide the benefits described herein, via a combination of general knowledge of the applicable field as well as routine experimentation where needed. By way of non-limiting example, the amount of voided latex particles in the composition of the invention may be in the range of from 0.1 to 10 solids weight %, preferably from 0.5 to 7.5 solids weight, based on the total weight of the composition.

The inventive skin care compositions contain inorganic metal oxide particles. Suitable inorganic metal oxides include, for example, zinc oxide (ZnO), titanium dioxide ($TiO_2$), and mixtures thereof. In certain embodiments, the inorganic metal oxide particles are pigment grade ZnO or pigment grade $TiO_2$. In certain embodiments, the inorganic metal oxide particles are transparent ZnO or transparent $TiO_2$. Most inorganic metal oxides used in sunscreen formulations produce a cosmetically undesirable white appearance caused by light scattering. Thus, as used herein, the term "transparent" inorganic metal oxide sunscreen particle refers to inorganic metal oxide particles produced by a variety of processing conditions which render compositions containing such particles as clear, or more transparent than pigment grade, upon application. The inorganic metal oxide particles may be uncoated or they may be surface treated. For instance, in some embodiments, the inorganic metal oxide particles are surface treated to provide hydrophobicity. In some embodiments, the inorganic metal oxide particles are surface treated with alumina, silica, or organic materials such as esters. In some embodiments, the inorganic metal oxide particles are surface treated with alumina, alumina and jojobo esters, or alumina, jojobo esters, and silica. In some embodiments, the inorganic metal oxide particles are surface treated with alumina but are free of silica and jojobo esters.

Suitable ZnO particles for use in the invention include, for example, those commercially available under the trade names Z-COTE from BASF Corporation, ZINCLEAR IM from Antaria Limited, and Z-CLEAR from Actifirm. Suitable $TiO_2$ particles include, for example, those commercially available under the trade names TIPAQUE and TTO-51(A) from Ishiharra Sangyo Kaisha, Ltd., T-COTE from BASF Corporation, UFTR (from Miyoshi Kasei), and SOLAVEIL CLARUS from Uniquema. In certain embodiments, the skin care compositions include inorganic metal oxide particles in an amount of from 0.1 to 20 weight %, preferably from 0.5 to 18 weight %, and more preferably from 0.5 to 10 weight %, by weight of the composition.

In some embodiments, the weight ratio of the copolymer particles to voided latex particles in the compositions of the inventions is in the range of 3:1 to 1:3, alternatively 2:1 to 1:2, alternatively 1.5:1 to 1:1, alternatively 1.25:1 to 1:1. In some embodiments, the weight ratio is 1.25:1 or alternatively it is 1:1. In some embodiments, the weight ratio of the copolymer particles, the voided latex particles, and the inorganic metal oxide particles is 1:1:1. In some embodiments, the weight ratio of the copolymer particles, the voided latex particles, and the inorganic metal oxide particles is 1.25:1:1.25.

Skin care compositions of the invention also include one or more dermatologically acceptable carriers. Such material is typically characterized as a carrier or a diluent that does not cause significant irritation to the skin and does not negate the activity and properties of active agent(s) in the composition. Examples of dermatologically acceptable carriers that are useful in the invention include, without limitation, water, such as deionized or distilled water, emulsions, such as oil-in-water or water-in-oil emulsions, alcohols, such as ethanol, isopropanol or the like, glycols, such as propylene glycol, glycerin or the like, creams, aqueous solutions, oils, ointments, pastes, gels, lotions, milks, foams, suspensions, powders, or mixtures thereof. In some embodiments, the composition contains from about 99.99 to about 50 percent by weight of the dermatologically acceptable carrier, based on the total weight of the composition.

The skin care compositions of the invention may also include sunscreen actives in addition to the inorganic metal oxide particles. Suitable additional sunscreen actives include, for example, para aminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, trolamine salicylate, titanium dioxide, zinc oxide, benzophenones, benzylidenes, salicylates, or other known UV filters, including diethanolamine methoxycinnamate, digalloy trioleate, ethyl dihydroxypropyl PABA, glyceryl aminobenzoate, and lawsone with dihydroxy acetone and red petrolatum.

The skin care compositions of the invention may also include other ingredients known in the art of sunscreen formulations including, for example, a thickener, emollients, an emulsifier, a humectant, a surfactant, a suspending agent, a film forming agent, a lower monoalcoholic polyol, a high boiling point solvent, a propellant, a mineral oil, silicon feel modifiers, or mixtures thereof. The amount of optional ingredients effective for achieving the desired property provided by such ingredients can be readily determined by one skilled in the art.

Other additives may be included in the compositions of the invention such as, but not limited to, abrasives, absorbents, aesthetic components such as fragrances, pigments, colorings/colorants, essential oils, skin sensates, astringents (e.g., clove oil, menthol, camphor, eucalyptus oil, eugenol, menthyl lactate, witch hazel distillate), preservatives, anti-caking agents, a foam building agent, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, and vitamins (e.g., Vitamin C) and derivatives thereof. The amount of option ingredients effective for achieving the desired property provided by such ingredients can be readily determined by one skilled in the art.

As noted above, skin care compositions of the present invention are highly effective as SPF and UV absorption boosters. Accordingly, the skin care compositions of the present invention are useful for the treatment and protection of skin, including, for example, protection from UV damage, moisturization of the skin, prevention and treatment of dry skin, protection of sensitive skin, improvement of skin tone and texture, masking imperfections, and inhibition of transepidermal water loss. Thus, in one aspect the present invention provides that the skin care compositions may be used in a method for protecting skin from UVA and UVB damage comprising topically administering to the skin a skin care composition as described herein. The compositions may also be used in a method for boosting the SPF or UV absorption of a sunscreen composition containing inorganic metal oxide particles and one or more dermatologically acceptable carriers by including in the composition copolymer particles voided latex particles as described herein. In certain embodiments, the inventive skin care compositions containing inorganic metal oxide particles and copolymer parties and voided latex particles as described herein have an SPF that is more than 25% higher, and preferably more than 50% higher, than compositions containing equivalent levels of unaltered inorganic metal oxide particles (i.e., not containing copolymer particles and voided latex particles).

In practicing the methods of the invention, the skin care compositions are generally administered topically by applying or spreading the compositions onto the skin. A person of ordinary skill in the art can readily determine the frequency with which the compositions should be applied. The frequency may depend, for example, on the level of exposure to UV light that an individual is likely to encounter in a given day and/or the sensitivity of the individual to UV light. By way of non-limiting example, administration on a frequency of at least once per day may be desirable.

Some embodiments of the invention will now be described in detail in the following Examples.

EXAMPLES

General
Preparation of Copolymer Particles Containing Phosphorus Acid Monomer:

Exemplary copolymer particles in accordance with the present invention contain the components recited in Table 1.

TABLE 1

Exemplary Copolymer Particles

| Sample | Monomer (wt %) |
|---|---|
| P3 | Stage 1 (35%): 11.2 BA/83.5 MMA/5.1 PEM/0.2 MAA<br>Stage 2 (65%): 14.1 BA/85.7 MMA/0.2 MAA |

MMA = methyl methacrylate
MAA = methacrylic acid
BA = butyl acrylate
PEM = phosphoethyl methacrylate
ALMA = allyl methacrylate Polymer P3 May be Prepared as Follows A Stage 1 monomer emulsion was prepared by mixing 65.5 g deionized (DI) water, 16.5 g (30% active) anionic surfactant-A (surfactant having an average composition of lauryl-(ethylene oxide)$_4$ sodium sulfate; 30 wt % solids), 27.6 g BA, 205.6 g MMA, 0.50 g MAA, and 12.6 g PEM. A Stage 2 monomer emulsion was then prepared by mixing 136 g DI water, 15.4 g (30% active) anionic surfactant A, 64.5 g BA, 392.2 g MMA, and 0.95 g MAA. A 3 liter reactor, four-necked round bottom flask equipped with a paddle stirrer, a thermocouple, nitrogen inlet, and reflux condenser was assembled. To the flask was added 1,170 g DI water and 16.5 g (30% active) anionic surfactant A, and stirring was started. The contents of the flask were heated to 84° C. under a nitrogen atmosphere. A solution of 1.4 g sodium persulfate (NaPS) in 13 g DI water was added. The stage 1 monomer emulsion was fed into the reactor over 40 minutes. A solution of 0.71 g NaPS in 43 g DI water was fed separately to the flask for 40 minutes. After the addition of Stage 1 monomer emulsion the container was rinsed with a small portion of DI water and added into the flask. The NaPS co-feed was stopped and the reaction held at 87° C. for 10 minutes. The Stage 2 monomer emulsion was fed into the flask over 65 minutes. The NaPS co-feed was re-started and fed for 65 minutes. Furthermore, a separate solution containing 5.3 g of ammonium hydroxide (28% solution), 20 g of water was fed over 65 minutes. After the addition of Stage 2 monomer emulsion the container was rinsed with a small portion of DI water and fed into the flask. The contents of the flask were maintained at 84-86° C. for 5 minutes. The batch was then cooled to 65° C. A redox pair of hydrogen peroxide aqueous solution and iso-ascorbic acid solution was fed into the kettle separately. The batch was cooled to room temperature.

TABLE 2

Preparation of Exemplary Voided Latex Particles (VLP-1):
Monomer (wt %)

| | |
|---|---|
| Core (4.7%): | 60 MMA/40 MAA |
| Shell 1 (22.1%): | 8.5 BMA/88.5 MMA/3 MAA |
| Shell 2 (26.8%): | 94.9 Sty/5.1 DVB |
| Shell 3 (46.4%): | 46.2 Sty/51.1 DVB/2.7 SSS |

MMA = methyl methacrylate
BMA = butyl methacrylate
MAA = methacrylic acid
Sty = styrene
DVB = divinylbenzene
SSS = sodium styrene sulfonate
SDBS—Sodium dodecylbenzenesulfonate To a 3-liter, 4-neck round bottom flask equipped with overhead stirrer, thermocouple, heating mantle, adapter inlet, Claisen head fitted with a water condenser and nitrogen inlet, and an inlet adapter, was added 875.3 grams (g) deionized water which was heated to 84° C. under nitrogen. To the heated water was added 0.30 g acetic acid, 1.70 g sodium persulfate in 15.5 g of deionized water followed by the addition of an aqueous dispersion of 31% poly(MMA/MAA//60/40) acrylic seed (core) polymer, having an average particle diameter of approximately 110 to 220 nm. To this heated mixture at 82° C., a monomer emulsion containing 71.5 g deionized water, 2.1 g aqueous solution of 23% SDBS, 91.6 g MMA, 8.9 g BMA and 3.1 g MAA was metered in over 90 minutes followed by a deionized water rinse. Next, a solution of 0.65 g sodium persulfate in 32.8 g deionized water was added over 90 minutes and the reaction temperature was raised to 90° C. concurrent with the addition of a second monomer emulsion containing 48.3 g deionized water, 0.35 g aqueous solution of 23% SDBS, 120.5 g Sty, 6.45 g DVB and 0.70 g linseed oil fatty acid over 30 minutes. At the completion of addition of the second monomer emulsion, 8.0 g aqueous 28% ammonium hydroxide was added, and hold for 10 min. To the reaction mixture at 91° C. was added, over 60 minutes, a third monomer emulsion containing 100.5 g deionized water, 1.0 g aqueous solution of 23% SDBS, 104.2 g Sty, 115.25 g DVB, and 6.1 g of sodium styrene sulfonate, followed by a deionized water rinse. The reactor contents were held at 91° C. for 30 minutes, then 5.8 g of aqueous solution containing 0.10 g of FeSO4.7H2O and 0.10 g of versene was added followed by the concurrent addition over 60 minutes of 5.10 g of t-butylhydrogen peroxide (70%) in 19.0 g of deionized water and 2.6 g isoascorbic acid in 19.0 g deionized water, to the reactor maintained at 91° C. The latex was cooled to room temperature and then filtered.

Tio₂ Powder:

TiO₂ powders used in the examples contain various types of surface treatment. Compositional details are provided in Table 3.

TABLE 3

Compositional breakdown of surface treated TiO₂

| Composition<br>% of Product TiO$_2$ | TiO$_2$-1[a] | TiO$_2$-2[b] | TiO$_2$-3[c] |
|---|---|---|---|
| Titanium Dioxide | 94.00-99.00 | 71.00-78.00 | 83.00-87.00 |
| Alumina | 1.00-4.00 | 13.00-16.00 | 0.75-3.00 |
| Jojoba Esters | | 7.00-9.00 | 4.00-6.00 |
| Silica | | | 2.50-7.00 |

[a]Available as TTO-80 from Kobo Products.
[b]Available as MPT-154-NJE8 from Kobo.
[c]Available as TEL-100-NJE5 from Kobo.

SPF Measurement Procedure:

The SPF value of formulations is measured using an in vitro technique substantially according to the following protocol in compliance with the COLIPA 2007 method:

Initially, the weight of a roughened PMMA substrate (purchased from SCHÖNBERG GmbH & Co. KG, Hamburg/Germany) is measured. The batch to be tested is then deposited on the substrate and then quickly leveled with a 7 micron draw down bar to achieve a thin, uniform layer. The layer is allowed to dry for about 20 minutes, and the weight of the substrate plus dry uniform layer is determined. The UV absorption of dry uniform layer is measured using a LAB SPHERE UV-2000S spectrometer at multiple points on the layer.

The percent solids of the layer is measured using an OHAUS MB45 solids analyzer. Using the weight of the dry film, and the solids content of the layer, the weight, and consequently the density of the original wet layer immediately after deposition can be calculated. Using this information, the SPF can be calculated by the following equation:

$$SPF = \frac{\int_{290nm}^{400nm} E(\lambda)S(\lambda)\partial\lambda}{\int_{290nm}^{400nm} E(\lambda)S(\lambda)10^{(-A(\lambda))}\partial\lambda}$$

Where $E(\lambda)$=spectral irradiance of the Standard Sun Spectrum; $S(\lambda)$=erythemal action spectrum at wavelength $\lambda$; and $A(\lambda)$=corrected spectral absorbance at wavelength $\lambda$ (a correction factor is calculated to extrapolate the data to establish what the absorbance would be at a wet layer density of 2.0 mg/cm² (using the original wet layer immediately after deposition).

Examples 1-4. SPF Performance with Different Surface Treated TiO₂

In this example, the boosting effect of the inventive polymers on the three types of TiO₂ surface treated materials (from Table 3) were tested for SPF performance. Data are shown in Table 4.

TABLE 4

| Example | Ingredients (amts in wt %) | TiO$_2$-1 | TiO$_2$-2 | TiO$_2$-3 |
|---|---|---|---|---|
| 1 (comparative) | 2.5 TiO₂ | 4.7 | 4.9 | 4.8 |
| 2 (comparative) | 2.5 TiO₂ + 2.5 Polymer P3 | 6.5 | 11.6 | 8.5 |
| 3 (comparative) | 2.5 TiO₂ + 2.5 VLP-1 | 11.4 | 5.5 | 5.0 |
| 4 (inventive) | 2.5% TiO₂ + 2.5 VLP-1 + 2.5 Polymer P3 | 23.3 | 16.2 | 7.7 |

Example 4 in Table 4 shows the boosting effect of the compositions of the invention on the SPF performance of TiO₂. In addition, Example 4 demonstrates a synergistic effect between the copolymer particles and the voided latex particles when used with alumina coated TiO₂ (TiO₂-1).

Preparation and Testing of Sunscreen Formulations

For the following examples 5-28, sunscreen formulations containing the components recited in Table 5 are prepared as described below.

TABLE 5

Sunscreen Formulations

| Phase | Formulation Number | A | B | C | D | E | F | G | H |
|---|---|---|---|---|---|---|---|---|---|
| A | Deionized Water | 82.55 | 82.05 | 81.55 | 81.05 | 74.35 | 73.85 | 73.35 | 72.85 |
| | EDTA | 0.05 | 0.05 | 0.05 | 0.05 | 0.05 | 0.05 | 0.05 | 0.05 |
| | Keltrol CGT | 0.5 | 0.5 | 0.5 | 0.5 | 0.5 | 0.5 | 0.5 | 0.5 |
| | Propylene Glycol | 1 | 1 | 1 | 1 | 1 | 1 | 1 | 1 |
| | Methyl Gluceth-10 | 1 | 1 | 1 | 1 | 1 | 1 | 1 | 1 |
| | Phenoxyethanol (and) Methylparaben (and) Isopropylparaben (and) Isobutylparaben (and) Butylparaben | 0.9 | 0.9 | 0.9 | 0.9 | 0.9 | 0.9 | 0.9 | 0.9 |
| | Voided Latex Particles (VLP-1) | 1 | 1.5 | 2 | 2.5 | 1 | 1.5 | 2 | 2.5 |

TABLE 5-continued

| | | Sunscreen Formulations | | | | | | | |
|---|---|---|---|---|---|---|---|---|---|
| Phase | Formulation Number | A | B | C | D | E | F | G | H |
| B | $TiO_2$-1/$TiO_2$-2/$TiO_2$-3 | 2.5 | 2.5 | 2.5 | 2.5 | 2.5 | 2.5 | 2.5 | 2.5 |
| | PEG 40 Stearate | 1 | 1 | 1 | 1 | 1 | 1 | 1 | 1 |
| | Glyceryl Stearate | 1 | 1 | 1 | 1 | 1 | 1 | 1 | 1 |
| | Cetearyl Alcohol | 3 | 3 | 3 | 3 | 3 | 3 | 3 | 3 |
| | C12-15 Alkyl Benzoate | 3.5 | 3.5 | 3.5 | 3.5 | 3.5 | 3.5 | 3.5 | 3.5 |
| | Dimethicone DC 200 | 2 | 2 | 2 | 2 | 2 | 2 | 2 | 2 |
| C | P3 Polymer (30.5% solids) | 0 | 0 | 0 | 0 | 8.2 | 8.2 | 8.2 | 8.2 |

Procedure: Mix Deionized water, EDTA, propylene glycol, and Methyl Gluceth-10 together and heat to 65° C. Add the Keltrol CGT (xanthan gum) slowly and stir at 500 RPMS until thickened. Add the phenoxyethanol, methylparaben, etc., mixture. Add the voided latex particles and stir until mixed. Add the Polymer P3. Increase temperature to 80° C. Mix all ingredients from Phase B in a separate vessel and heat to 75-80° C. until all waxes are melted. Optionally, add $TiO_2$ to Phase A and stir until there is a uniform mixture. Increase stirring of Phase A to 1000 RPM's. Add Phase B to Phase A. Stir for 5 minutes at 75-80° C. Remove from heat and let cool while stirring at 800-1000 RPMS. Optionally add Phase C when formulation is cooled at 40° C. Homogenize for 10 minutes when at room temperature. It should be noted that the $TiO_2$ may be added at various points during the procedure with the ultimate goal of providing homogenous formulations. Such point may be determined by a person of ordinary skill in the art without undue experimentation. For instance, it may be preferable to add a hydrophilic $TiO_2$ to Phase A, prior to the addition of Phase B to A. On the other hand, if the $TiO_2$ is hydrophobic, it may be preferable to add it to the mixture of Phase A and Phase B.

Examples 5-12. SPF Boosting Effect on Hydrophobically Coated $TiO_2$-1 Particles The SPF values of inventive compositions with $TiO_2$-1 type particles at varying amounts of the voided latex particles, as well as comparative compositions, are shown in Table 6.

TABLE 6

| | | Testing on $TiO_2$-1 | | | |
|---|---|---|---|---|---|
| Example | Formulation | $TiO_2$-1 (wt %) | Polymer P3 (wt %) | VLP-1 (wt %) | SPF |
| | Control | 2.5 | 0 | 0 | 4.68 |
| | Control | 5 | 0 | 0 | 11.52 |
| 5 (comparative) | A | 2.5 | 0 | 1 | 5.21 |
| 6 (comparative) | B | 2.5 | 0 | 1.5 | 4.9 |
| 7 (comparative) | C | 2.5 | 0 | 2 | 9.29 |
| 8 (comparative) | D | 2.5 | 0 | 2.5 | 11.4 |
| 9 (inventive) | E | 2.5 | 2.5 | 1 | 6.21 |
| 10 (inventive) | F | 2.5 | 2.5 | 1.5 | 7.53 |
| 11 (inventive) | G | 2.5 | 2.5 | 2 | 11.62 |
| 12 (inventive) | H | 2.5 | 2.5 | 2.5 | 23.3 |

The Data in Table 6 shows that the inventive compositions are effective at increasing the SPF efficacy of $TiO_2$ particles of type $TiO_2$-1. The data shows a particularly enhanced effect with Example 12, containing a ratio of copolymer particles to voided latex particles of 1:1.

Examples 13-20. SPF Boosting Effect on Hydrophobically Coated $TiO_2$-2 Particles The SPF values of inventive compositions with $TiO_2$-2 type particles at varying amounts of the voided latex particles, as well as comparative compositions, are shown in Table 7.

TABLE 7

| | | Testing on $TiO_2$-2 | | | |
|---|---|---|---|---|---|
| Example | Formulation | $TiO_2$-2 (wt %) | Polymer P3 (wt %) | VLP-1 (wt %) | SPF |
| | Control | 2.5 | 0 | 0 | 4.9 |
| | Control | 5 | 0 | 0 | 15.7 |
| 13 (comparative) | A | 2.5 | 0 | 1 | 5.3 |
| 14 (comparative) | B | 2.5 | 0 | 1.5 | 6.4 |
| 15 (comparative) | C | 2.5 | 0 | 2 | 4.9 |
| 16 (comparative) | D | 2.5 | 0 | 2.5 | 5.5 |
| 17 (inventive) | E | 2.5 | 2.5 | 1 | 5.9 |
| 18 (inventive) | F | 2.5 | 2.5 | 1.5 | 6.9 |
| 19 (inventive) | G | 2.5 | 2.5 | 2 | 10.3 |
| 20 (inventive) | H | 2.5 | 2.5 | 2.5 | 16.2 |

The Data in Table 7 shows that the inventive compositions are effective at increasing the SPF efficacy of $TiO_2$ particles of type $TiO_2$-2. The data shows a particularly enhanced effect with Example 20, containing a ratio of copolymer particles to voided latex particles of 1:1.

Examples 21-28 SPF Boosting Effect on Hydrophobically Coated $TiO_2$-3 Particles The SPF values of inventive compositions with $TiO_2$-3 type particles at varying amounts of the voided latex particles, as well as comparative compositions, are shown in Table 8.

TABLE 8

| | | Testing on $TiO_2$-3 | | | |
|---|---|---|---|---|---|
| Example | Formulation | $TiO_2$-3 (wt %) | Polymer P3 (wt %) | VLP-1 (wt %) | SPF |
| | Control | 2.5 | 0 | 0 | 6.1 |
| | Control | 5 | 0 | 0 | 9.1 |
| 21 (comparative) | A | 2.5 | 0 | 1 | 6.1 |

TABLE 8-continued

Testing on TiO$_2$-3

| Example | Formulation | TiO$_2$-3 (wt %) | Polymer P3 (wt %) | VLP-1 (wt %) | SPF |
|---|---|---|---|---|---|
| 22 (comparative) | B | 2.5 | 0 | 1.5 | 8.1 |
| 23 (comparative) | C | 2.5 | 0 | 2 | 12.1 |
| 24 (comparative) | D | 2.5 | 0 | 2.5 | 5.0 |
| 25 (inventive) | E | 2.5 | 2.5 | 1 | 14.0 |
| 26 (inventive) | F | 2.5 | 2.5 | 1.5 | 10.3 |
| 27 (inventive) | G | 2.5 | 2.5 | 2 | 21.5 |
| 28 (inventive) | H | 2.5 | 2.5 | 2.5 | 7.7 |

The Data in Table 8 shows that the inventive compositions are effective at increasing the SPF efficacy of TiO$_2$ particles of type TiO$_2$-3. The data shows a particularly enhanced effect with Example 27, containing a ratio of copolymer particles to voided latex particles of 1.25:1.

What is claimed is:
1. A skin care composition comprising:
   (a) copolymer particles comprising, based on the total weight of the copolymer particles, polymerized units derived from
      (i) 0.1 to 20 weight % of phosphorus acid monomers, and
      (ii) 80 to 99.9 weight % of comonomers, wherein the comonomers are selected from the group consisting of styrene, butadiene, α-methyl styrene, vinyl toluene, vinyl naphthalene, ethylene, propylene, vinyl acetate, vinyl versatate, vinyl chloride, vinylidene chloride, acrylonitrile, methacrylonitrile, (meth)acrylamide, methyl (meth)acrylate, ethyl (meth)acrylate, n-butyl (meth)acrylate, 2-ethylhexyl (meth)acrylate, cyclohexyl (meth)acrylate, n-octyl (meth)acrylate, n-decyl (meth)acrylate, n-dodecyl (meth)acrylate, tetradecyl (meth)acrylate, lauryl (meth)acrylate, oleyl (meth)acrylate, palmityl (meth)acrylate, stearyl (meth)acrylate, isobornyl (meth)acrylate, benzyl (meth)acrylate, phenyl (meth)acrylate, 2-bromoethyl (meth)acrylate, 2-phenylethyl (meth)acrylate, 1-naphthyl (meth)acrylate), ethoxyethyl (meth)acrylate, ethyl maleate, dimethyl fumarate, trimethyl aconitate, ethyl methyl itaconate, (meth)acrylic acid, itaconic acid, fumaric acid, maleic acid and mixtures thereof;
   (b) voided latex particles comprising:
      (i) at least one core polymer comprising polymerized units derived from (a) 20 to 60 weight % of monoethylenically unsaturated monomers containing at least one carboxylic acid group, based on the total weight of the core polymer, wherein the monoethylenically unsaturated monomers containing at least one carboxylic acid group of the core polymer comprise a monomer selected from the group consisting of (meth)acrylic acid, (meth)acryloxypropionic acid, itaconic acid, aconitic acid, maleic acid, maleic anhydride, fumaric acid, cronotic acid, citraconic acid, maleic anhydride, monomethyl maleate, monomethyl fumarate, monomethyl itaconate, and mixtures thereof; and (b) 40 to 80 weight % of non-ionic ethylenically unsaturated monomers, based on the total weight of the core polymer; wherein the non-ionic ethylenically unsaturated monomers are selected from the group consisting of styrene, vinyltoluene, ethylene, vinyl acetate, vinyl chloride, vinylidene chloride acrylonitrile, (meth)acrylamide, methyl (meth)acrylate, ethyl (meth)acrylate, butyl (meth)acrylate, 2-ethylhexyl (meth)acrylate, benzyl (meth)acrylate, lauryl (meth)acrylate, oleyl (meth)acrylate, palmityl (meth)acrylate, stearyl (meth)acrylate, and mixtures thereof; and
      (ii) at least one shell polymer comprising polymerized units derived from (a) 55 to 85 weight % of non-ionic ethylenically unsaturated monomers, based on the total weight of the shell polymer; wherein the non-ionic ethylenically unsaturated monomers are selected from the group consisting of vinyl acetate, acrylonitrile, methacrylonitrile, nitrogen containing ring compound unsaturated monomers, styrene, α-methylstyrene, vinyltoluene, t-butylstyrene, ethylvinylbenzene, chlorostyrene, 3,5-bis(trifuoromethyl) styrene, ethylenic monomers, methyl acrylate, methyl methacrylate, ethyl acrylate, ethyl methacrylate, butyl acrylate, butyl methacrylate, isobutyl acrylate, isobutyl methacrylate, hydroxyethyl methacrylate, hydroxypropyl methacrylate, dimethylaminoethyl methacrylate, dimethylaminopropyl methacrylamide and mixtures thereof; and (b) 15 to 45 weight % of polyethylenically unsaturated monomers, based on the total weight of the shell polymer; wherein the polyethylenically unsaturated monomers are selected from the group consisting of di(meth)acrylates, tri(meth)acrylates, tetra(meth)acrylates, polyallylic monomers, diethyleneglycol divinyl ether, divinylbenzene, divinyl ketone, divinylpyridine, divinyl sulfide, divinyl sulfone, divinyltoluene, divinylxylene, glycerol trivinyl ether, trivinylbenzene, 1,2,4-trivinylcyclohexane, N,N'-ethylenebisacrylamide, partially fluorinated α,ω-dienes, trifluoroalkadienes, trifluorodivinylbenzenes, fluorinated divinyl ethers of fluorinated 1,2-ethanediol, acrylate ester of neopentyl glycol monodicyclopentenyl ether, allyl acryloxypropionate, allyl acrylate, allyl methacrylate, crotyl acrylate, crotyl methacrylate, 3-cyclohexenylmethyleneoxyethyl acrylate, 3-cyclohexenylmethyleneoxyethyl methacrylate, dicyclopentadienyloxyethyl acrylate, dicyclopentadienyloxyethyl methacrylate, dicyclopentenyl acrylate, dicyclopentenyl methacrylate, dicyclopentenyloxyethyl acrylate, dicyclo pentenyloxyethyl methacrylate, methacrylate ester of neopentyl glycol monodicyclopentenyl ether, methallyl acrylate, trimethylolpropane diallyl ether monoacrylate, trimethylolpropane diallyl ether monomethacrylate, N-allyl acrylamide and mixtures thereof;
   wherein the voided latex particles contain a void and have a particle size of from 50 nm to 1000 nm;
   (c) inorganic metal oxide particles, wherein the inorganic metal oxide particles are selected from the group consisting of transparent zinc oxide, transparent titanium dioxide and mixtures thereof; and
   (d) one or more dermatologically acceptable carriers.
2. The skin care composition of claim 1 comprising:
   from 0.1 to 30 weight % of the copolymer particles;
   from 0.1 to 10 weight % of the voided latex particles;

from 0.1 to 20 weight % of the inorganic metal oxide particles; and balance one or more dermatologically acceptable carriers, each based on the total weight of the composition.

3. The skin care composition of claim 1, wherein the phosphorus acid monomers comprise phosphoethyl methacrylate.

4. The skin care composition of claim 1, wherein the comonomers comprise at least one of butyl acrylate, methyl methacrylate, and methacrylic acid.

5. The skin care composition of claim 1, wherein
the non-ionic ethylenically unsaturated monomers of the at least one shell polymer comprise a monomer selected from the group consisting of methyl acrylate, methyl methacrylate, butyl methacrylate styrene, and mixtures thereof, and
the polyethylenically unsaturated monomers of the at least one shell polymer comprise divinylbenzene.

6. The skin care composition of claim 1, wherein
the monoethylenically unsaturated monomers containing at least one carboxylic acid group of the core polymer comprise a monomer selected from the group consisting of acrylic acid, methacrylic acid and mixtures thereof, and
the non-ionic ethylenically unsaturated monomers of the core polymer comprise a monomer selected from the group consisting of methyl methacrylate, butyl methacrylate and mixtures thereof.

7. The skin care composition of claim 1, wherein the at least one shell polymer further comprises polymerized units derived from 0.1 to 5 weight % of a monoethylenically unsaturated monomer containing at least one carboxylic acid group; wherein the monoethylenically unsaturated monomer containing at least one carboxylic acid group is selected from the group consisting of (meth)acrylic acid, (meth)acryloxypropionic acid, itaconic acid, aconitic acid, maleic acid, fumaric acid, crotonic acid, citraconic acid, maleic anhydride monomethyl maleate, monomethyl fumarate and monomethyl itaconate.

8. The skin care composition of claim 1, wherein the at least one shell polymer further comprises polymerized units derived from 0.1 to 5 weight % of a monoethylenically unsaturated monomer containing at least one non-carboxylic acid group; wherein the monoethylenically unsaturated monomer containing at least one non-carboxylic acid group is selected from the group consisting of allylsulfonic acid, allylphosphonic acid, allyloxybenzenesulfonic acid, 2-acrylamido-2-methylpropanesulfonic acid ("AMPS"), 2-hydroxy-3-(2-propenyloxy)propanesulfonic acid, 2-methyl-2-propene-1-sulfonic acid, 2-methacrylamido-2-methyl-1-propanesulfonic acid, 3-methacrylamido-2-hydroxy-1-propanesulfonic acid, 3-sulfopropyl acrylate, 3-sulfopropyl methacrylate, isopropenylphosphonic acid, vinylphosphonic acid, phosphoethyl methacrylate, styrenesulfonic acid, vinylsulfonic acid and the alkali metal and ammonium salts thereof.

9. A method of boosting the SPF or UV absorption of a skin care composition containing inorganic metal oxide particles, wherein the inorganic metal oxide particles are selected from the group consisting of transparent zinc oxide, transparent titanium dioxide and mixtures thereof; and one or more dermatologically acceptable carriers, the method comprising including in the skin care composition:
(a) copolymer particles comprising, based on the total weight of the copolymer particles, polymerized units derived from (i) 0.1 to 20 weight % of phosphorus acid monomers, and
(ii) 80 to 99.9 weight % of comonomers, wherein the comonomers are selected from the group consisting of styrene, butadiene, α-methyl styrene, vinyl toluene, vinyl naphthalene, ethylene, propylene, vinyl acetate, vinyl versatate, vinyl chloride, vinylidene chloride, acrylonitrile, methacrylonitrile, (meth)acrylamide, methyl (meth)acrylate, ethyl (meth)acrylate, n-butyl (meth)acrylate, 2-ethylhexyl (meth)acrylate, cyclohexyl (meth)acrylate, n-octyl (meth)acrylate, n-decyl (meth)acrylate, n-dodecyl (meth)acrylate, tetradecyl (meth)acrylate, lauryl (meth)acrylate, oleyl (meth)acrylate, palmityl (meth)acrylate, stearyl (meth)acrylate, isobornyl (meth)acrylate, benzyl (meth)acrylate, phenyl (meth)acrylate, 2-bromoethyl (meth)acrylate, 2-phenylethyl (meth)acrylate, 1-naphthyl (meth)acrylate), ethoxyethyl (meth)acrylate, ethyl maleate, dimethyl fumarate, trimethyl aconitate, ethyl methyl itaconate, (meth)acrylic acid, itaconic acid, fumaric acid, maleic acid and mixtures thereof;
(b) voided latex particles comprising:
(i) at least one core polymer comprising polymerized units derived from (a) 20 to 60 weight % of monoethylenically unsaturated monomers containing at least one carboxylic acid group, based on the total weight of the core polymer, wherein the monoethylenically unsaturated monomers containing at least one carboxylic acid group of the core polymer comprise a monomer selected from the group consisting of (meth)acrylic acid, (meth)acryloxypropionic acid, itaconic acid, aconitic acid, maleic acid, maleic anhydride, fumaric acid, cronotic acid, citraconic acid, maleic anhydride, monomethyl maleate, monomethyl fumarate, monomethyl itaconate, and mixtures thereof; and (b) 40 to 80 weight % of non-ionic ethylenically unsaturated monomers, based on the total weight of the core polymer; wherein the non-ionic ethylenically unsaturated monomers are selected from the group consisting of styrene, vinyltoluene, ethylene, vinyl acetate, vinyl chloride, vinylidene chloride acrylonitrile, (meth)acrylamide, methyl (meth)acrylate, ethyl (meth)acrylate, butyl (meth)acrylate, 2-ethylhexyl (meth)acrylate, benzyl (meth)acrylate, lauryl (meth)acrylate, oleyl (meth)acrylate, palmityl (meth)acrylate, stearyl (meth)acrylate, and mixtures thereof; and
(ii) at least one shell polymer comprising polymerized units derived from (a) 55 to 85 weight % of non-ionic ethylenically unsaturated monomers, based on the total weight of the shell polymer; wherein the non-ionic ethylenically unsaturated monomers are selected from the group consisting of vinyl acetate, acrylonitrile, methacrylonitrile, nitrogen containing compound unsaturated monomers, styrene, α-methylstyrene, vinyltoluene, t-butylstyrene, ethylvinylbenzene, chlorostyrene, 3,5-bis(trifluoromethyl)styrene, ethylenic monomers, methyl acrylate, methyl methacrylate, ethyl acrylate, ethyl methacrylate, butyl acrylate, butyl methacrylate, isobutyl acrylate, isobutyl methacrylate, hydroxyethyl methacrylate, hydroxypropyl methacrylate, dimethylaminoethyl methacrylate, dimethylaminopropyl methacrylamide and mixtures thereof; and (b) 15 to 45 weight % of polyethylenically unsaturated monomers, based on the total weight of the shell polymer; wherein the polyethylenically unsaturated monomers are selected from the group consisting of di(meth)acrylates, tri(meth)acrylates, tetra(meth)acrylates, polyallylic monomers, diethyleneglycol divinyl ether, divinylbenzene, divinyl ketone, divinylpyridine, divinyl sulfide, divinyl sulfone, divinyltoluene, divinylxylene, glycerol trivinyl ether, trivinylbenzene, 1,2,4-trivinylcyclohexane, N,N'-ethylenebisacrylamide, partially fluorinated $\alpha,\omega$-dienes, trifluoroalkadienes, trifluorodivinylbenzenes, fluorinated divinyl ethers of fluorinated 1,2-ethanediol, acrylate ester of neopentyl glycol monodicyclopentenyl ether, allyl acryloxypropionate, allyl acrylate, allyl methacrylate, crotyl acrylate, crotyl methacrylate, 3-cyclohexenylmethyleneoxyethyl acrylate, 3-cyclohexenylmethyleneoxyethyl methacrylate, dicyclopentadienyloxyethyl acrylate, dicyclopentadienyloxyethyl methacrylate, dicyclopentenyl acrylate, dicyclopentenyl methacrylate, dicyclopentenyloxyethyl acrylate, dicyclo pentenyloxyethyl methacrylate, methacrylate ester of neopentyl glycol monodicyclopentenyl ether, methallyl acrylate, trimethylolpropane diallyl ether mono-acrylate, trimethylolpropane diallyl ether mono-methacrylate, N-allyl acrylamide and mixtures thereof;
wherein the voided latex particles contain a void and have a particle size of from 50 nm to 1000 nm.

\* \* \* \* \*